United States Patent
Richardson (10) Patent No.: US 7,591,849 B2
(45) Date of Patent: Sep. 22, 2009

(54) MULTI-COMPONENT ACCOMMODATIVE INTRAOCULAR LENS WITH COMPRESSIBLE HAPTIC

(75) Inventor: Gary A. Richardson, Rochester, NY (US)

(73) Assignee: Bausch & Lomb Incorpoted, Rochester, NY (US)

( * ) Notice: Subject to any disclaimer, the term of this patent is extended or adjusted under 35 U.S.C. 154(b) by 0 days.

(21) Appl. No.: 11/173,704

(22) Filed: Jul. 1, 2005

(65) Prior Publication Data

US 2007/0005136 A1    Jan. 4, 2007

(51) Int. Cl.
*A61F 2/16* (2006.01)

(52) U.S. Cl. .................. 623/6.47; 623/6.34; 623/6.39

(58) Field of Classification Search ............... 623/6.34, 623/6.39, 6.4, 6.43, 6.46, 6.47
See application file for complete search history.

(56) References Cited

U.S. PATENT DOCUMENTS

| | | | |
|---|---|---|---|
| 4,253,199 A | 3/1981 | Banko |
| 4,254,509 A | 3/1981 | Tennant |
| 4,271,841 A | 6/1981 | Friedman |
| 4,298,996 A | 11/1981 | Barnet |
| 4,373,218 A | 2/1983 | Schachar |
| 4,409,691 A | 10/1983 | Levy |
| 4,426,741 A | 1/1984 | Bittner |
| 4,463,458 A | 8/1984 | Seidner |
| 4,517,138 A | 5/1985 | Rawlings et al. |
| 4,517,139 A | 5/1985 | Rawlings et al. |
| 4,556,998 A | 12/1985 | Siepser |
| 4,575,373 A | 3/1986 | Johnson |
| 4,603,697 A | 8/1986 | Kamerling |
| 4,666,445 A | 5/1987 | Tillay |
| 4,680,149 A | 7/1987 | Rawlings et al. |
| 4,710,193 A | 12/1987 | Volk |
| 4,720,286 A | 1/1988 | Bailey et al. |
| 4,790,847 A | 12/1988 | Woods |
| 4,816,031 A | 3/1989 | Pfoff |
| 4,842,601 A | 6/1989 | Smith |
| 4,888,012 A | 12/1989 | Hora et al. |

(Continued)

FOREIGN PATENT DOCUMENTS

DE    19501444 A1    7/1996

(Continued)

OTHER PUBLICATIONS

McLeod et al., "A dual optic accommodating foldable intraocular lens," Br J Ophthalmol, 2003, p. 1083-1085.

(Continued)

*Primary Examiner*—William H. Matthews (57) ABSTRACT

A multi-component accommodating intraocular lens (A-IOL) for implantation in a capsular bag of an eye having an optical axis, includes an anterior optical element and a posterior component that are connected by at least one compressible haptic. The compressible haptic, by definition, has a deformation feature that is resiliently deformable. The deformation feature allows the nominal overall diameter of the A-IOL to dynamically vary over a selected range in response to a capsular bag dimension that is different than that of an average population value, or in response to a change in the size and/or shape of the capsular bag due to post-operative capsular bag shrinkage, without substantially changing the separation distance between the anterior and posterior components of the A-IOL absent an intended accommodating force. Methods are also disclosed.

34 Claims, 6 Drawing Sheets

U.S. PATENT DOCUMENTS

| | | | |
|---|---|---|---|
| 4,892,543 A | 1/1990 | Turley |
| 4,902,293 A | 2/1990 | Feaster |
| 4,946,469 A | 8/1990 | Sarfarazi |
| 4,963,148 A | 10/1990 | Sulc et al. |
| 4,976,732 A | 12/1990 | Vorosmarthy |
| 4,989,605 A | 2/1991 | Rossen |
| 4,994,080 A | 2/1991 | Shepard |
| 4,994,082 A | 2/1991 | Richards et al. |
| 5,047,051 A | 9/1991 | Cumming |
| 5,076,683 A | 12/1991 | Glick |
| 5,108,429 A | 4/1992 | Wiley |
| 5,109,846 A | 5/1992 | Thomas |
| 5,152,789 A | 10/1992 | Willis |
| 5,173,723 A | 12/1992 | Volk |
| 5,201,762 A | 4/1993 | Hauber |
| 5,203,788 A | 4/1993 | Wiley |
| 5,275,623 A | 1/1994 | Sarfarazi |
| 5,275,624 A | 1/1994 | Hara et al. |
| 5,300,262 A | 4/1994 | Glick |
| 5,326,347 A | 7/1994 | Cumming |
| 5,360,438 A | 11/1994 | Fisher |
| 5,376,115 A | 12/1994 | Jansen |
| 5,391,202 A | 2/1995 | Lipshitz et al. |
| RE34,998 E | 7/1995 | Langerman |
| 5,476,514 A | 12/1995 | Cumming |
| 5,489,299 A | 2/1996 | Schachar |
| 5,489,302 A | 2/1996 | Skottun |
| 5,496,355 A | 3/1996 | Lipsky |
| 5,496,366 A | 3/1996 | Cumming |
| 5,593,436 A | 1/1997 | Langerman |
| 5,607,472 A | 3/1997 | Thompson |
| 5,620,720 A | 4/1997 | Glick et al. |
| 5,628,795 A | 5/1997 | Langerman |
| 5,674,282 A | 10/1997 | Cumming |
| 5,728,155 A | 3/1998 | Anello et al. |
| 5,769,890 A | 6/1998 | McDonald |
| 5,782,894 A | 7/1998 | Israel |
| 5,843,188 A | 12/1998 | McDonald |
| 6,013,101 A | 1/2000 | Israel |
| 6,051,024 A | 4/2000 | Cumming |
| 6,096,078 A | 8/2000 | McDonald |
| 6,117,171 A | 9/2000 | Skottun |
| 6,136,026 A | 10/2000 | Israel |
| 6,176,878 B1 | 1/2001 | Gwon et al. |
| 6,193,750 B1 | 2/2001 | Cumming |
| 6,197,059 B1 | 3/2001 | Cumming |
| 6,200,342 B1 | 3/2001 | Tassignon |
| 6,217,612 B1 | 4/2001 | Woods |
| 6,231,603 B1 | 5/2001 | Lang et al. |
| 6,299,641 B1 | 10/2001 | Woods |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,413,276 B1 | 7/2002 | Werblin |
| 6,423,094 B1 | 7/2002 | Sarfarazi |
| 6,428,573 B2 | 8/2002 | Barnett |
| 6,428,574 B1 | 8/2002 | Valunin et al. |
| 6,443,985 B1 | 9/2002 | Woods |
| 6,464,725 B2 | 10/2002 | Skotton |
| 6,478,821 B1 | 11/2002 | Laguette et al. |
| 6,485,516 B2 | 11/2002 | Boehm |
| 6,488,708 B2 | 12/2002 | Sarfarazi |
| 6,551,354 B1 | 4/2003 | Ghazizadeh et al. |
| 6,558,420 B2 | 5/2003 | Green |
| 6,616,691 B1 | 9/2003 | Tran |
| 6,616,692 B1 | 9/2003 | Glick et al. |
| 6,695,881 B2 | 2/2004 | Peng et al. |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,158 B2 | 11/2004 | Pham et al. |
| 6,846,326 B2 | 1/2005 | Zadno-Azizi et al. |
| 6,858,040 B2 | 2/2005 | Nguyen et al. |
| 6,884,261 B2 | 4/2005 | Zadno-Azizi et al. |
| 6,899,732 B2 | 5/2005 | Zadno-Azizi et al. |
| 7,041,134 B2 | 5/2006 | Nguyen et al. |
| 7,087,080 B2 | 8/2006 | Zadno-Azizi et al. |
| 7,118,596 B2 | 10/2006 | Zadno-Azizi et al. |
| 2002/0116057 A1 | 8/2002 | Ting et al. |
| 2002/0161434 A1 | 10/2002 | Laguette et al. |
| 2003/0018384 A1 | 1/2003 | Valyunin et al. |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi et al. |
| 2003/0130732 A1 | 7/2003 | Sarfarazi |
| 2003/0149480 A1 | 8/2003 | Shadduck |
| 2003/0187504 A1 | 10/2003 | Weinschenk, III et al. |
| 2004/0015236 A1 | 1/2004 | Sarfarazi |
| 2004/0111152 A1 | 6/2004 | Kelman |
| 2004/0160575 A1 | 8/2004 | Ayton et al. |
| 2004/0162612 A1 | 8/2004 | Portney et al. |
| 2004/0249455 A1 | 12/2004 | Tran |
| 2005/0021139 A1 | 1/2005 | Shadduck |
| 2005/0049700 A1 | 3/2005 | Zadno-Azizi et al. |
| 2005/0165410 A1 | 7/2005 | Zadno-Azizi et al. |
| 2005/0182419 A1 | 8/2005 | Tsai |
| 2005/0228401 A1 | 10/2005 | Zadno-Azizi et al. |
| 2005/0234547 A1 | 10/2005 | Nguyen et al. |
| 2005/0267575 A1 | 12/2005 | Nguyen et al. |
| 2006/0100703 A1 | 5/2006 | Evans et al. |
| 2006/0184244 A1 | 8/2006 | Nguyen et al. |
| 2007/0032866 A1 | 2/2007 | Portney |

FOREIGN PATENT DOCUMENTS

| | | |
|---|---|---|
| EP | 0162573 A2 | 11/1985 |
| EP | 0329981 A1 | 8/1989 |
| EP | 0337390 A2 | 10/1989 |
| EP | 0478929 A1 | 4/1992 |
| EP | 0336877 B1 | 10/1993 |
| EP | 0592813 A1 | 4/1994 |
| EP | 0328117 B1 | 12/1994 |
| EP | 0698381 A1 | 2/1996 |
| EP | 0507292 B1 | 7/1997 |
| FR | 2784575 B1 | 4/2000 |
| JP | 02126847 A | 5/1990 |
| WO | WO 96/16780 A2 | 6/1996 |
| WO | WO 99/20206 A1 | 4/1999 |
| WO | WO 00/04849 A1 | 2/2000 |
| WO | WO 01/19289 A1 | 3/2001 |
| WO | WO 01/34067 A1 | 5/2001 |
| WO | WO 01/64136 A2 | 9/2001 |
| WO | WO 02/071983 A1 | 9/2002 |
| WO | WO 03/000154 A2 | 1/2003 |

OTHER PUBLICATIONS

Schachar, "Cause and treatment of presbyopia with a method for increasing the amplitude of accommodation," Ann Ophthalmol, 1992, p. 445-452.

Schachar et al., "Experimental support for Schachar's hypothesis of accommodation," Ann of Ophthalmol, Nov. 1993, vol. 25 (No. 11), p. 404-409.

Adler-Grinberg, "Questioning our classical understanding of accommodation and presbyopia," Amer J of Optometry & Physiol Optics, 1986, vol. 63 (No. 7), p. 571-580.

Schachar, "Zonular Function: A new hypothesis with clinical implications," Ann Ophthalmol, 1994, p. 36-38.

Koretz et al., "How the human eye focuses," Scientific American, Jul. 1988, p. 92-99.

Hara et al., "Accommodative intraocular lens with spring action part 1. Design and placement in an excised animal eye," Ophthal Surgery, Feb. 1990, vol. 21 (No. 2), p. 128-133.

Hara et al., "Accommodative intraocular lens with spring action—Part 2. Fixation in the living rabbit," Ophthal Surgery, Sep. 1992, vol. 23 (No. 9), p. 632-635.

Cimberle, "Three accommodative IOLs show high-quality surface on SEM," Ocular Surgery News, p. 18-19, (Aug. 15, 2002).

MULTI-COMPONENT ACCOMMODATIVE INTRAOCULAR LENS WITH COMPRESSIBLE HAPTIC

FIELD OF THE INVENTION

Embodiments of the invention are generally directed to the field of accommodating intraocular lenses and, more particularly, to a multi-component accommodating intraocular lens and methods for improved design of the lens, and function and fit of the lens within the capsular bag.

BACKGROUND OF THE INVENTION

Figure 1:
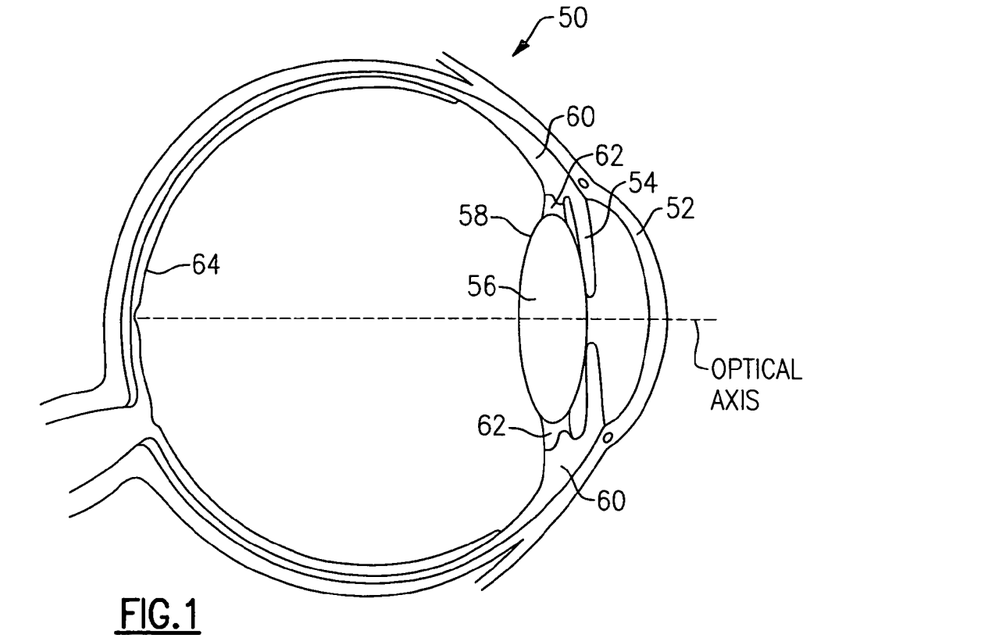
FIG. 1 is a cross sectional view of the human eye illustrating the natural crystalline lens in an unaccommodated state.
Figure 2:
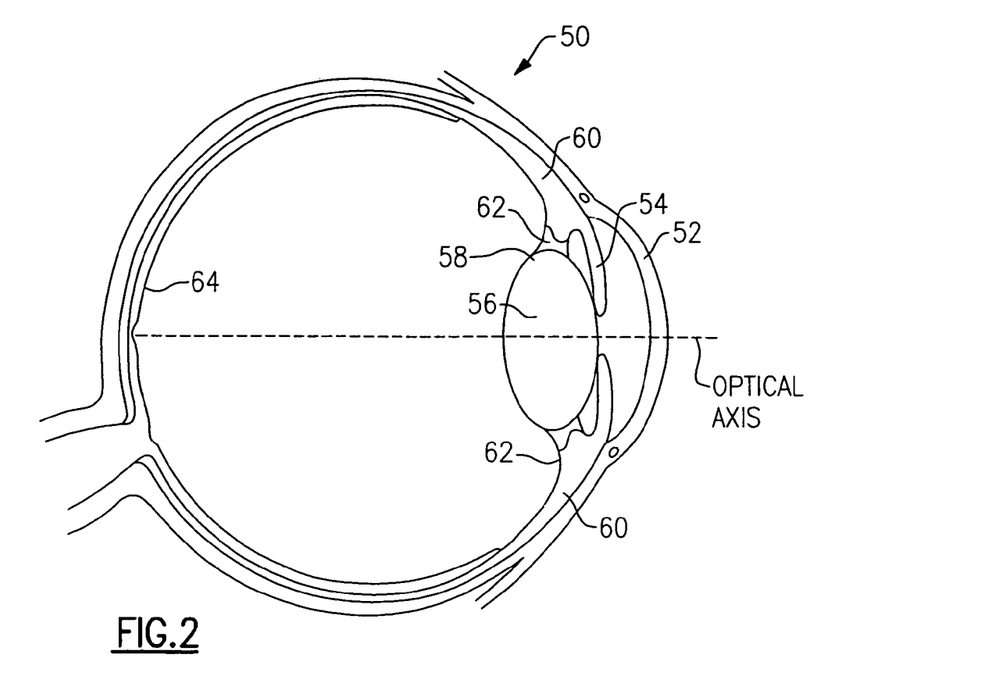
FIG. 2 is a cross sectional view of the human eye illustrating the natural crystalline lens in an accommodated state.

FIGS. 1 and 2 show the human eye 50 in section. The cornea 52, the iris 54 and the natural crystalline lens 56, which is situated within the elastic, membranous capsular bag or lens capsule 58, are specifically illustrated for a more thorough understanding of the invention. The capsular bag 58 is surrounded by and suspended within the ciliary muscle 60 by ligament-like structures called zonules 62.

As light enters the eye 50, the cornea 52 and the lens 56 cooperate to focus the incoming light and form an image on the retina 64 at the rear of the eye to facilitate vision. During the process known as accommodation, the shape of the lens 56 is altered (and its refractive properties thereby adjusted) to allow the eye 50 to focus on objects at varying distances. A typical healthy eye has sufficient accommodation to enable focused vision of objects ranging in distance from infinity (generally defined as over 20 feet from the eye) to very near (closer than 10 inches).

The crystalline lens 56 has a natural elasticity, and in its relaxed state assumes a shape that in cross-section resembles that of a football. Accommodation occurs when the ciliary muscle 60 moves the lens from its relaxed or "unaccommodated" state (shown in FIG. 1) to a contracted or "accommodated" state (shown in FIG. 2). Movement of the ciliary muscle 60 to the relaxed/unaccommodated state increases tension in the zonules 62 and capsular bag 58, which in turn causes the lens 56 to take on a thinner (as measured along the optical axis) or taller shape as shown in FIG. 1. In contrast, when the ciliary muscle 60 is in the contracted/accommodated state, tension in the zonules 62 and capsular bag 58 is decreased and the lens 56 takes on the fatter or shorter shape as shown in FIG. 2. When the ciliary muscles 60 contract and the capsular bag 58 and zonules 62 slacken, some degree of tension is maintained in the capsular bag 58 and zonules 62.

In response to various physiological conditions, the most notable being the occurrence of cataracts, the natural crystalline lens may have to be removed. It is often replaced by an intraocular lens (IOL). Since the natural lens accounts for the eye's ability to accommodate, as described above, the implantation of an accommodating IOL is intended to re-establish this ability (to a lesser or greater degree) and eliminate the need for additional lenses such as spectacles, for example, for focusing near-vision objects. Accommodating IOLs typically consist of a single optical element, but multi-component (two or more optical elements) accommodating IOLs are in development. A two-element accommodating IOL, for example, will generally provide more focusing power and accommodative range than a single-element accommodating IOL. Embodiments of the current invention are advantageously directed to a two-element accommodating intraocular lens referred to herein as the A-IOL.

The accommodative operation of the A-IOL is similar to that described above for the natural crystalline lens. The A-IOL replaces the natural lens and thus is disposed within the evacuated capsular bag. The A-IOL includes an anterior (front or closer to the cornea) optic and a posterior (back or closer to the retina) optic. Depending upon the particular design of the A-IOL, the anterior and posterior optics are connected by a biasing structure that generally serves three primary functions: i) biasing the position of one optic relative to the other in a natural, most-spaced-apart, accommodating state of the A-IOL; ii) allowing the anterior optic to translate axially relative to the posterior optic in response to a force exerted by the ciliary muscle and zonules acting on the capsular bag; and iii) fitting/securing the A-IOL in the capsular bag so that it remains aligned and able to function properly in the eye over an extended period of time. This biasing structure is referred to as a haptic (one or more), a bridge, a connector, and other terms widely recognized in the art. As described in greater detail below, the biasing structure according to embodiments of the present invention include one or more deformation features that allow the biasing structure to be compressed. According to the embodiments of the invention disclosed and claimed herein, this biasing structure will be referred to as a 'compressible haptic'.

With respect to multi-component A-IOLs, one view in the field is that the biasing structure should consistently conform to the inner dimensions (shape and size) of the capsular bag and be able to slide rather than stick to the interior of the bag. A non-conforming or sticky lens fit, for example, may adversely impact lens performance, ocular physiology and wearer comfort. Another concern with the design and development of A-IOLs is their ability to conform to capsular bags of a diameter smaller than they are intended to be compatible with. However, capsular bag dimensions are known to vary among the IOL-receiving population. Currently, capsular bag dimensions in live subjects are not accurately measurable. In addition, it is known that the capsular bag shrinks post-operatively after natural lens removal and bag evacuation. These conditions are believed by some to have negative effects on the ability of known A-IOL lens designs to maintain their shape in the eye and deliver the requisite performance.

Accordingly, the inventor has recognized a need for improvements in design and construction of multi-component accommodating IOLs to account for population variation in capsular bag dimensions and/or post-operative bag shrinkage. Embodiments of the invention described herein below will describe such improvements and illustrate the benefits associated therewith.

SUMMARY OF THE INVENTION

Embodiments of the present invention are directed to A-IOLs that are capable of adapting to different capsular bag dimensions among the population and/or to post-traumatic capsular bag changes in size and/or shape, without affecting the accommodative characteristics of the A-IOL.

The A-IOL embodiments described herein below are "two-element" A-IOLs. However, it is to be appreciated that aspects of the present invention may be applied to any suitable two component A-IOLs. In this regard, it is to be understood that a posterior optic in any of the described embodiments may be replaced by a non-optical (non-refracting or non-diffracting) element. For example, embodiments may include a clear aperture in a posterior component structure, without modifying the nature of the compressible haptic feature of the invention that will be described in greater detail below. Thus, in every aspect, the anterior and posterior components will be coupled by a compressible haptic.

For purposes of clarity and accuracy, the following terms, definitions and meanings will be applied to the embodiments throughout the description. The A-IOL will be described as having a nominal overall (outer) diameter, D. D refers to the maximum circumferential outside diameter of the lens 'as molded'; i.e., in the mold. In the mold, the lens components are in their spaced-apart (non-axially compressed, accommodating) state. In other words, D is the outer diameter of the circumference defined by a radius originating on the optical axis and extending to the outermost radial point of the biasing structure, as molded. When the lens components are axially translated to be as close to one another as permitted by the particular A-IOL design, the haptics may bulge to some degree, in which case the circumferential outer diameter of the lens will have a value greater than D, referred to herein as $D_{max}$. Similarly, for an exemplary silicone A-IOL, if the A-IOL is set on a flat horizontal surface with its posterior component down and supporting the weight of the A-IOL, the measured outer circumferential diameter of the A-IOL may be slightly larger than the nominal overall diameter, D, due to the effect of gravity and the stiffness characteristics of the A-IOL.

As stated above, according to the embodiments of the invention, the A-IOL includes at least one 'compressible haptic'. The term 'compressible haptic' as used herein is defined as a biasing structure that joins the anterior and posterior optics, and having at least one deformation feature that allows the nominal overall diameter, D, of the A-IOL to dynamically vary between D and a reduced diameter value, referred to as $D_{min}$, without imparting any axial, translational movement to the optics. This definition applies to the A-IOL in its natural, spaced-apart, accommodated state. As mentioned, the overall diameter, $D_{max}$, of the lens in a non-accommodated state may be greater than the nominal overall diameter value D; however, it will be appreciated that a certain diameter reduction from the $D_{max}$ value will be afforded by the compressible haptic under conditions that similarly effect the diameter reduction when the A-IOL is in the spaced-apart condition. The deformation feature of the compressible haptic allows the nominal overall diameter, D, of the A-IOL to vary to the $D_{min}$ value in response to implanting the A-IOL into a capsular bag that is, for example, slightly smaller than that for an average population value, or into a bag that shrinks post-operatively.

Having defined these terms above, an embodiment of the invention is directed to a method for making a two-component accommodating intraocular lens (A-IOL), in which the nominal overall diameter, D, of the A-IOL is dynamically variable between D and a reduced diameter value, $D_{min}$, in response to, for example, capsular bag dimension variation and/or post-operative bag shrinkage, without effecting translational movement between the anterior and posterior lens components over the change in nominal overall diameter of the A-IOL between $D_{min}$ and D, absent an intended accommodating force. The method involves providing the A-IOL having an anterior optic, a posterior component and at least one compressible haptic that couples at least a portion of the anterior optic and at least a portion of the posterior component, providing a deformation feature in the at least one compressible haptic, such that a nominal overall diameter, D, of the A-IOL can vary over a range between D and a $D_{min}$ value less than D when the deformation feature is varied between an undeformed state and a deformed state, without changing a separation distance between the anterior optic and the posterior component over the range. According to an aspect, the method involves providing the at least one deformation feature such that $D_{min}$ is in the range between about 8 to 10 millimeters. A more particular aspect involves providing the at least one deformation feature such that $D_{min}$ is in the range between about 8 to 9.5 millimeters. According to another aspect, the method comprises providing the at least one deformation feature such that $D_{min}$ is in the range of between about 80% to 95% of the nominal overall diameter of the A-IOL. In another aspect, the method involves providing the at least one deformation feature adjacent a posterior region of the at least one compressible haptic. Alternatively, the at least one deformation feature can be provided adjacent an anterior region of the at least one compressible haptic. In a further alternative aspect, a plurality of the at least one deformation feature can be located, respectively, adjacent an anterior end region of the at least one compressible haptic and a posterior end region of the at least one compressible haptic. In another aspect, the at least one deformation feature can be located in either an anterior translation member or a posterior translation member of the at least one compressible haptic.

A multi-optic accommodating intraocular lens (A-IOL) for implantation in a capsular bag of an eye, according to an embodiment of the invention, includes an anterior optic, a posterior component and at least one compressible haptic that joins at least a portion of the anterior optic and at least a portion of the posterior component. In an as-molded state, the A-IOL has a nominal overall (outside) diameter, D, defined by the extrapolated circumferential diameter of the A-IOL, as described above. The at least one compressible haptic includes a deformation feature that is resiliently deformable. The deformation feature allows the nominal overall diameter, D, of the A-IOL to vary between D and a reduced diameter value, $D_{min}$, due to reduced capsular bag dimensions, while leaving substantially unchanged the optical component separation distance, absent an intended accommodating process force. Although this occurs in the natural, accommodated state of the lens, the A-IOL diameter may similarly vary between a value $D_{max}$ and a lesser diameter value greater than $D_{min}$ when the eye is not accommodating. In a reduced diameter state, the deformation feature will be said to be in a deformed state. It is to be understood that the term 'deformed state' refers solely to the condition of the deformation feature of the compressible haptic and not to a change in A-IOL thickness or optic/component separation distance due to the accommodative properties of the A-IOL effected by the ciliary process.

In an exemplary aspect, the deformation feature will be located adjacent the anterior optic. It may alternatively be located adjacent the posterior optic/component. The deformation feature may be disposed intermediate the anterior and posterior components, however, this may be less advantageous if the translational movement of the A-IOL is effected by the central region of the haptic. Illustratively, the deformation feature is a semi-continuous gap; i.e., the compressible haptic is continuous between the anterior optic and the posterior component but has a gap region that can deform. Exemplary shapes of the gap include a squared or rounded U-shape, a V-shape, a C-shape, a W-shape, a J-shape, an M-shape, an N-shape, an S-shape and others that function to allow the deformation feature to deform and, thus, the nominal overall diameter, D, of the A-IOL to vary over a selected range in response to variation in bag dimensions. In various aspects, the at least one compressible haptic may be one continuous piece or may comprise two, three, four or more piece-wise compressible haptics distributed about the anterior and posterior optics; that is, a plurality of unitary compressible haptics. In an alternative aspect, each one or more of the compressible haptics may include two or more sections that can be connected together after implantation of the A-IOL. One or more of the sections will include a deformation feature to allow nominal overall diameter variation as described above. According to an aspect, the deformation feature of the compressible haptic is configured and arranged to act as a hard stop that operates to limit the minimum optic separation distance of the A-IOL.

The A-IOL embodiments described above, as well as the compressible haptics and the optical components, can be manufactured by known techniques including, but not limited to, molding and casting. The materials used for the A-IOL and its component structures, whether of completely unitary construction or multi-element construction, comprise known materials for manufacturing A-IOLs including, but not limited to, silicone formulations, polymethylmethacrylate (PMMA) and other suitable materials that provide visual clarity, refractive capability, biocompatibility and mechanical stability. The optical characteristics of A-IOLs according to the embodiments of the invention are not part of the invention per se. As such, lens power distribution, lens shapes, translation ranges and other parameters can be selected to suit patient and manufacturing requirements.

The various benefits and advantages of the A-IOL embodiments of the invention will be evident to a person skilled in the art in view of the drawing figures and the following detailed description, and as defined in the appended claims.

DETAILED DESCRIPTION OF AN EMBODIMENT OF THE INVENTION

Figure 3:
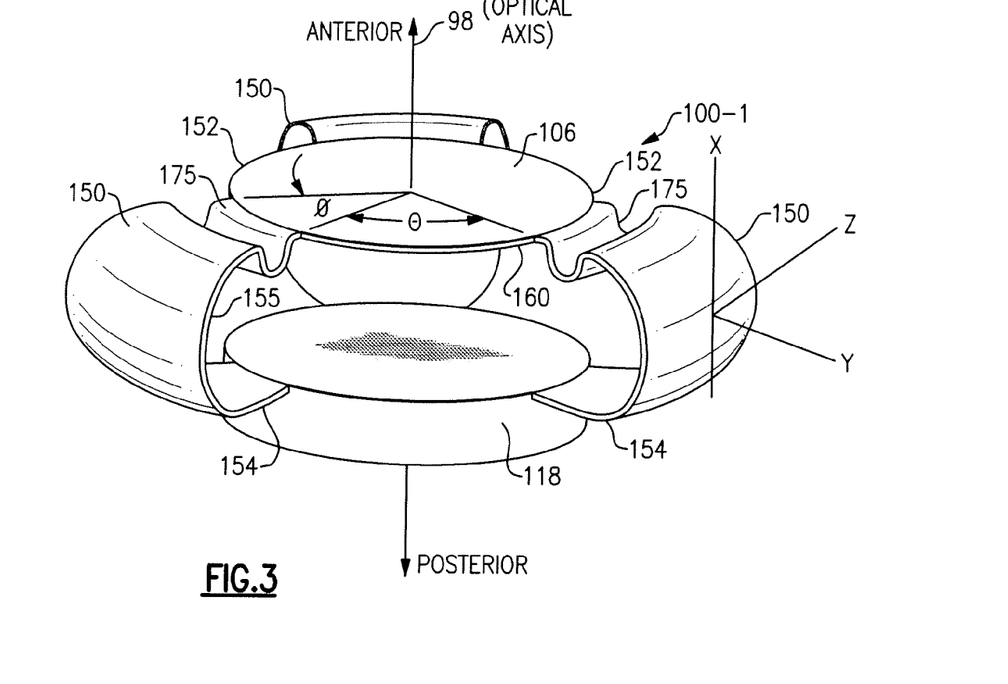
FIG. 3 is an isometric view of an A-IOL according to an exemplary embodiment of the invention.
Figure 4A:
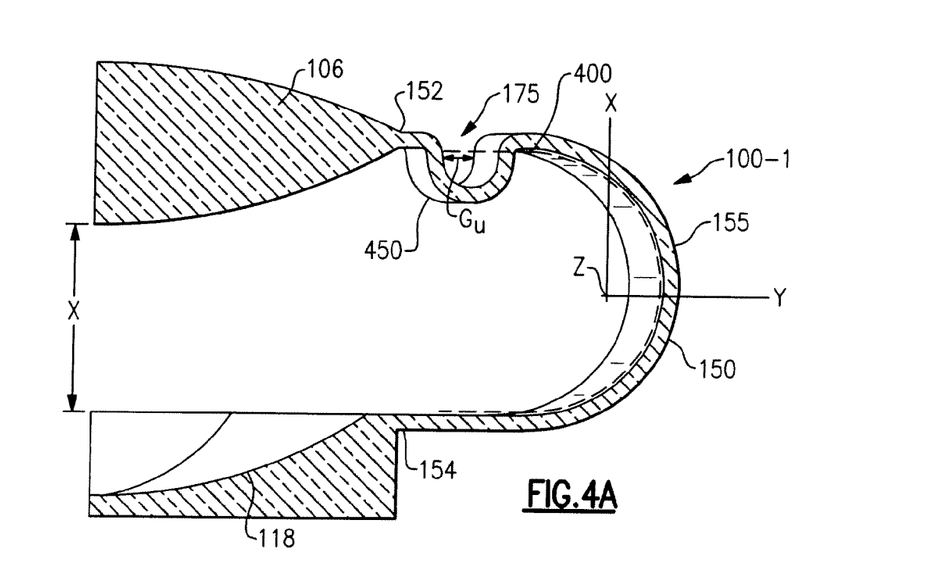
FIG. 4A is a cross sectional schematic view of the exemplary A-IOL of FIG. 3 in an undeformed state.

FIGS. 3 and 4A depict an exemplary embodiment of an A-IOL 100-1, which is configured for implantation into an evacuated capsular bag 58 (FIGS. 1, 2) in place of the natural lens 56, and is further configured to change the refractive properties of the eye in response to the eye's natural process of accommodation. A Cartesian coordinate system is shown in FIG. 3 to orient the reader, as the optical axis of the A-IOL as shown would be aligned with optical axis of a patient's eye. This coordinate system is depicted purely to facilitate the description herein; thus, it is not intended to limit the possible orientations that the A-IOL may assume during use. For example, the A-IOL 100-1 may rotate about, or may be displaced along, the optical axis during use without detracting from the performance of the lens system. The terms "anterior" and "posterior" refer to the depicted directions on the optical axis 98 of the A-IOL 100-1. When the A-IOL 100-1 is implanted in an eye, the anterior direction extends toward the cornea and the posterior direction extends toward the retina.

The two-optic A-IOL 100-1 shown in FIG. 3 includes an anterior optic 106, a posterior optic 118 and three single-piece compressible haptics 150, which join the anterior and posterior optics and facilitate translational movement of the anterior optic along the optical axis 98. It will be understood that when the A-IOL is implanted, the posterior optic is intended to remain stationary in the posterior region of the capsular bag, while the anterior optic translates along the optical axis for accommodative effect. Each of the compressible haptics 150 has an anterior end region 152 that joins at least a portion of the periphery 160 of the anterior optic 106. The compressible haptics also have a posterior end region 154 that joins at least a portion of the periphery 165 of the posterior optic 118. The compressible haptics 150 further have a central region 155 that extends between the anterior end region 152 and the posterior end region 154.

As shown in FIG. 3, the three compressible haptics 150 are spaced equidistantly about the periphery of the optical components. In alternative aspects, two compressible haptics or four or more compressible haptics may be provided. In another alternative aspect, a single compressible haptic may be joined continuously about the peripheral edges of the anterior and posterior optics. An underlying consideration is that the compressible haptic(s) be flexible enough to enable relatively unrestricted accommodative movement of the anterior optic relative to the posterior optic in response to the ciliary process, while simultaneously being stiff enough to support the A-IOL in visual axial alignment within the capsular bag. Accordingly, the cross sectional profile shape of the compressible haptic may alternatively be circular, apical, or of other curvilinear variation. Regardless, as described herein above, the outermost extrapolated circumference of the compressible haptic(s) in the as-molded state defines the nominal overall diameter, D, of the A-IOL in its natural, accommodative, spaced-apart condition.

According to an exemplary embodiment, the nominal overall diameter, D, of the A-IOL 100-1 is in the range between about 9.0 to 9.7 mm due to molding tolerances. In an exemplary aspect, the nominal overall diameter value, D, is about 9.5 mm. Empirical data associated with cadaver eyes suggests that the average major diameter of the capsular bag among the population is between about 8.5 to 10.5 mm and, perhaps, between about 9 to 10 mm. Work with cadaver eyes also indicated that the A-IOL 100-1 having an as-molded nominal overall diameter, D, of about 9.5 mm provided the best overall fit in the capsular bag.

Figure 4B:
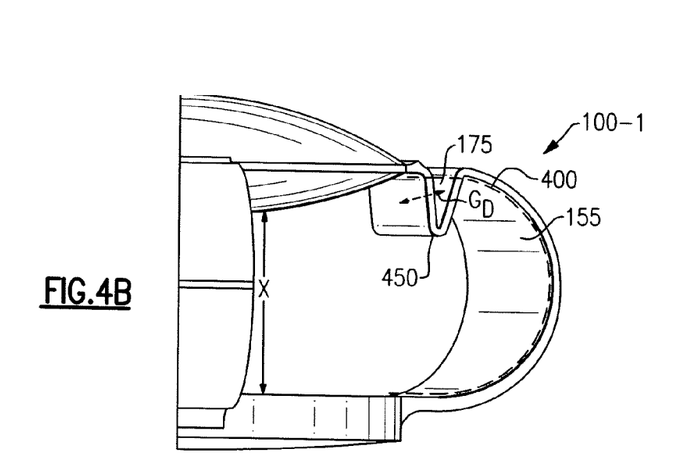
FIG. 4B is a cross sectional schematic view of the exemplary A-IOL of FIG. 3 in a deformed state.

As shown in FIGS. 3, 4A, and 4B, each compressible haptic 150 has at least one deformation feature 175 that provides a dynamic alteration of the nominal overall diameter of the A-IOL in response to capsular bag size variation. In the exemplary A-IOL 100-1, each deformation feature 175, in the form of a semi-continuous gap, is located adjacent the anterior end portion 152 of the respective compressible haptic 150. If, for example, the bag size of the patient receiving the A-IOL is in the smaller range of the average population, upon implantation of the A-IOL the deformation feature 175 will deform as shown in FIG. 4B to provide a gap dimension, GD, that is less than an undeformed gap dimension, GU (described in greater detail below), providing the A-IOL 100-1 with a reduced nominal overall diameter, Dmin, while at the same time leaving the axial separation distance, X, between the anterior optic and the posterior optic substantially unchanged. An inner surface of the compressible haptic, exclusive of said deformation feature 175, defining an inner profile 400 is illustrated in FIGS. 4A and 4B. A valley 450 of said deformation feature extends radially inwardly of said inner profile.

Figure 7A:
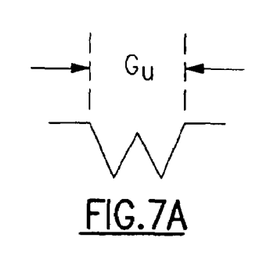
FIGS. 7A-E show exemplary gap shapes of a deformation feature of a compressible haptic according to aspects of an embodiment of the invention.
Figure 7B:
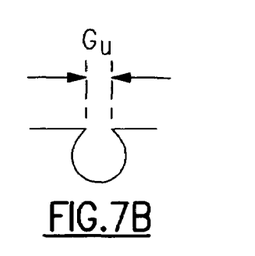
Figure 7C:
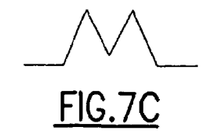
Figure 7D:
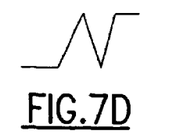
Figure 7E:
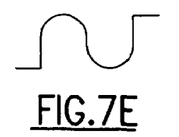

As shown in FIGS. 7A and 7B, in conjunction with FIGS. 3 and 4A, each deformation feature 175 has an undeformed gap dimension GU. The value of GU is selected to provide the A-IOL 100-1 with a reduced nominal overall diameter, Dmin, of between about 80% to 95% of the (undeformed) nominal overall diameter D. In an exemplary aspect, each deformation feature has an undeformed gap dimension, GU, in the range between about 500 to 1000 microns (μ). In a more particular aspect, GU is on the order of about 750μ. In a further exemplary aspect, the diameter variation range between D and Dmin will be about 0.5 to 1.0 millimeters (mm). In a further exemplary aspect, Dmin will be in the range between about 8 mm to 10 mm and, more particularly, between about 8.5 mm to 9.5 mm.

In an illustrative aspect, the deformation feature 175 is in the form of a semi-continuous, U-shaped gap. Other gap shapes may include, for example, C-shaped, J-shaped, V-shaped, W-shaped, M-shaped, N-shaped, S-shaped, as illustrated in FIGS. 7A-E, which enable suitable resilient radial deformation of the compressible haptic in order to dynamically vary the nominal overall diameter of the A-IOL over a selected range in response to a particular capsular bag dimension or a post-implant change in capsular bag dimensions. Deformation features according to embodiments of the invention are not limited to the specific gap shapes disclosed above. A person skilled in the art will appreciate that other structural forms and shaped may likewise provide the radial deformation of the A-IOL as described above.

Figure 5:
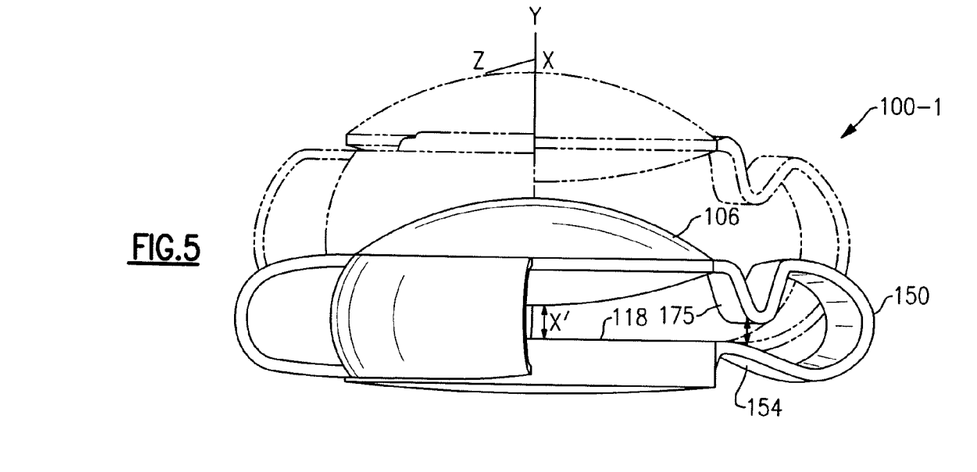
FIG. 5 is a cross sectional schematic view of an exemplary A-IOL illustrating a deformation feature configured and arranged to operate as a hard stop of a compressible haptics according to an exemplary aspect of the invention.
Figure 6A:
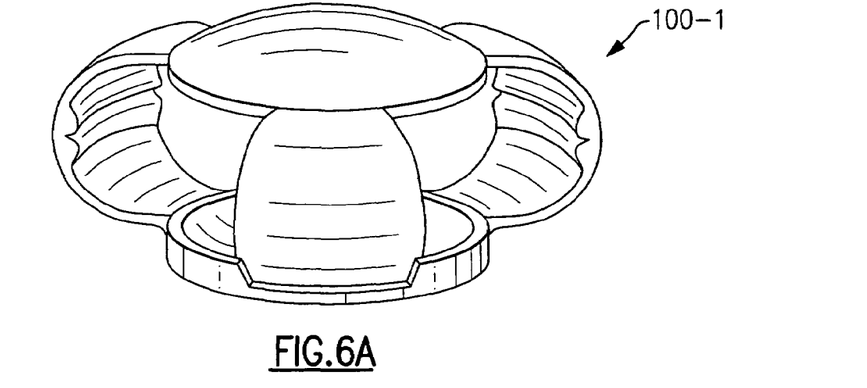
FIG. 6A is a perspective view of another exemplary A-IOL aspect of the invention.
Figure 6B:
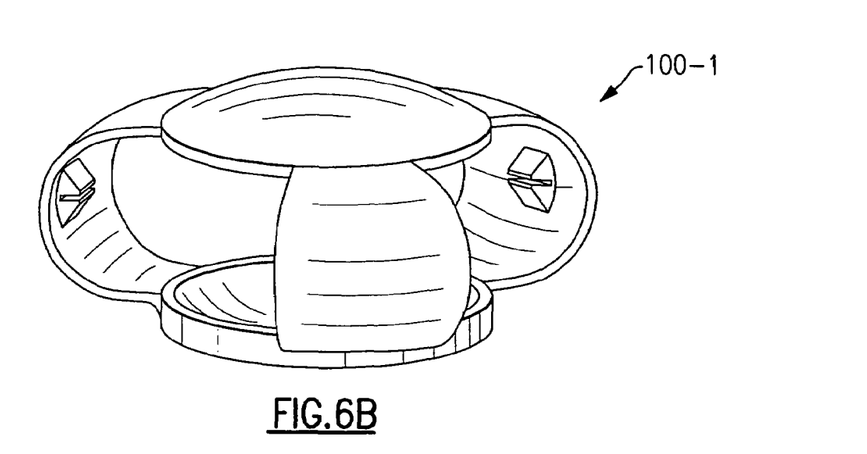
FIG. 6B is a perspective view of another exemplary A-IOL aspect of the invention.

FIG. 5 shows an exemplary aspect of A-IOL 100-1 in which the deformation feature 175 is configured to operate as a hard stop. When the ciliary process relaxes, the zonules tense, bringing the A-IOL into an unaccommodated state; i.e., the anterior optic 106 is moved closer to the posterior optic 118. It is desirable to maintain a minimum optic separation distance, x', that is greater than zero to avoid lens touching and possible anterior/posterior lens sticking. The deformation feature 175 can be designed to limit axial lens compression to a desired minimum amount, such as about 1 mm, in an exemplary aspect. Lens shapes, types and other physical considerations of the A-IOL will largely determine the actual minimum lens separation distance, which may be lesser or greater than 1 mm. As shown in FIG. 5 for reasons of viewer clarity, the bottom region of the deformation feature 175 is not in physical contact with the posterior portion 154 of the compressible haptic 150. However, it is to be appreciated that deformation feature 175 contacts the posterior end region 154 to limit axial compression.

As illustrated in FIGS. 3, 4A, 5, 6A and 6B, the deformation feature 175 may be located adjacent the posterior end region of the compressible haptic, at both the anterior and posterior end regions of the compressible haptic or at another location, e.g., central region, within the compressible haptic such that the nominal overall diameter of the A-IOL can vary as described above.

With the exception of the deformation feature 175, the exemplary A-IOL 100-1 is modeled after an embodiment of what is known in the industry as the Sarfarazi elliptical accommodative intraocular lens. The referenced embodiment of the Sarfarazi lens is disclosed in U.S. Pat. Nos. 5,275,623; 6,423,094; 6,488,708; and U.S. Published Application Nos. 2004/0015236 and 2003/0130732, the disclosures of which are incorporated by reference in their entireties to the fullest extent allowed by applicable laws and rules.

In an exemplary embodiment, the A-IOL 100-1 has the following parameters:
  power range: 18-22 D;
  overall nominal diameter: 9.50 mm
  optic body diameter: 5.50 mm;
  anterior clear optic diameter: 5.50 mm;
  posterior clear optic diameter: 5.00 mm (5.00 mm dia. anterior surface);
  posterior optic center thickness: 0.200 mm;
  compressible haptic thickness: 0.150 mm;
  haptic-to-haptic separation: 2.80 mm.

The anterior optic is bi-convex and has an aspheric anterior surface. The posterior optic has negative power. Various lens shape combinations are possible, including concave-plano, concave-convex, convex-concave, biconex, aspheric and others. The A-IOL may be fabricated from various materials including silicone compositions, polymethylmethacrylate (PMMA) or other materials that provide visual clarity, refractive capability, biocompatibility and mechanical stability. The compressible haptics may be connected to the peripheral edges of the anterior and posterior optics by staking, integral formation, gluing, or other known techniques.

In an illustrative aspect, the three compressible haptics subtend an angle Ø of 30-40 degrees at the optics' peripheries as viewed in a direction of line of sight and extend outwardly to form a nominal diameter D of approximately 9-9.5 mm in diameter. It is to be appreciated that said diameter D approximates the normal internal diameter of the capsular bag of the human eye. The compressible haptic is generally elliptical in plan view and has arcuate end region surfaces for attachment to the periphery of the anterior and posterior optics. In cross section, the haptics are arcuate and have a radius of curvature of approximately 4.5 mm, which enables the haptics to smoothly conform to the anterior surface of an evacuated capsular bag.

Figure 8A:
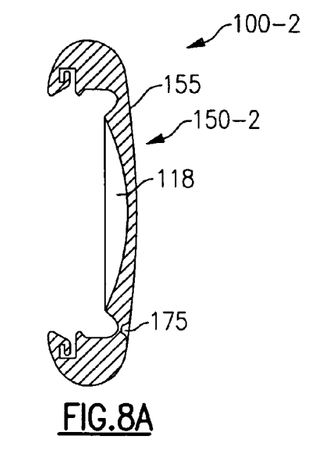
FIGS. 8A and 8B are cross sectional views of a two piece compressible haptic according to an exemplary embodiment of the invention.
Figure 8B:
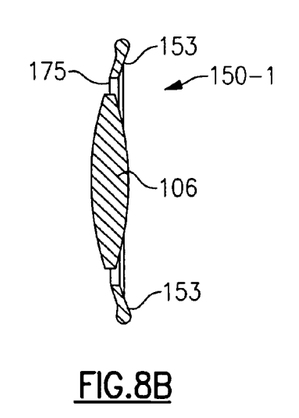

Although the exemplary A-IOL 100-1 is a unitary, cast-molded accommodating intraocular lens of the Sarfarazi type, embodiments of the invention are not so limited in terms of piece-wise design, construction, production or in-vivo parameters. For example, as shown in FIGS. 8A, 8B, A-IOL 100-2 includes an anterior portion 153 of a two-piece compressible haptic 150-1/150-2 connected to the anterior optic 106, and a posterior portion 155 connected to the posterior optic 118. Either or both of the anterior and posterior portions 153, 155 may incorporate a deformation feature 175 that provides the A-IOL 100-2 with a dynamically variable nominal overall diameter as described above. The anterior and posterior portions 153, 155 can be connected during lens implantation. A-IOL 100-2 is modeled after an embodiment of the intraocular lens described in U.S. Pat. No. 6,695,881, the disclosure of which is fully incorporated herein by reference to the fullest extent allowed by applicable laws and rules.

Figure 9:
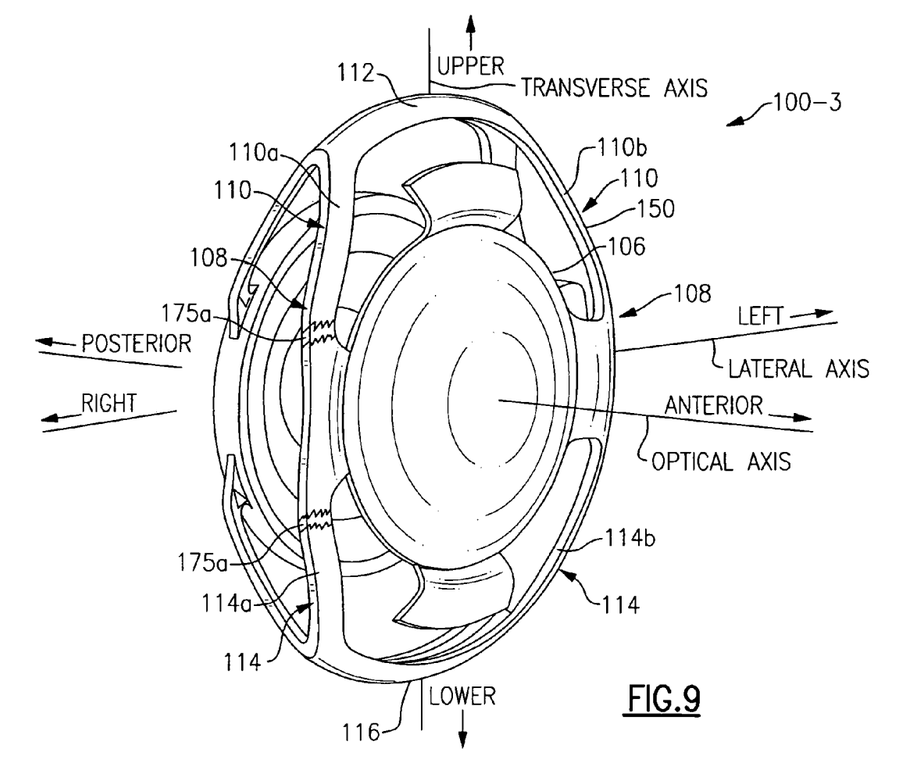
FIG. 9 is a perspective view of another A-IOL aspect of an exemplary embodiment of the invention.
Figure 10:
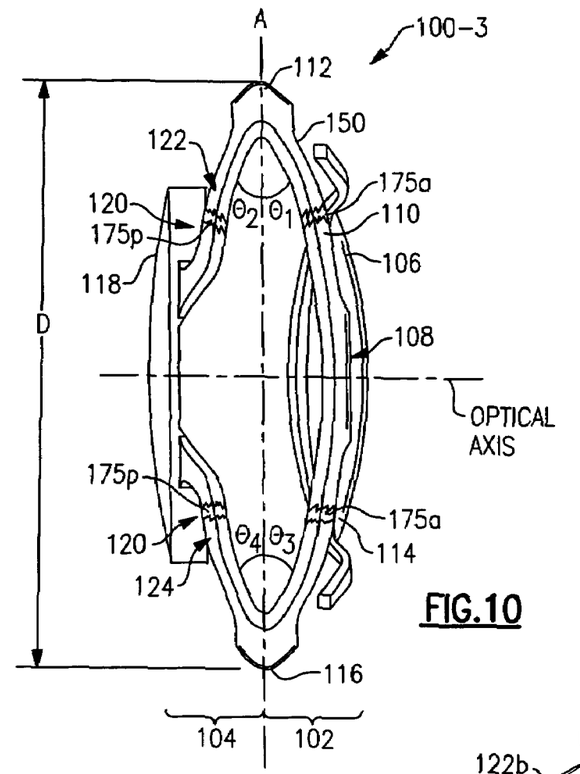
FIG. 10 is a side view of the A-IOL illustrated in FIG. 8.
Figure 11:
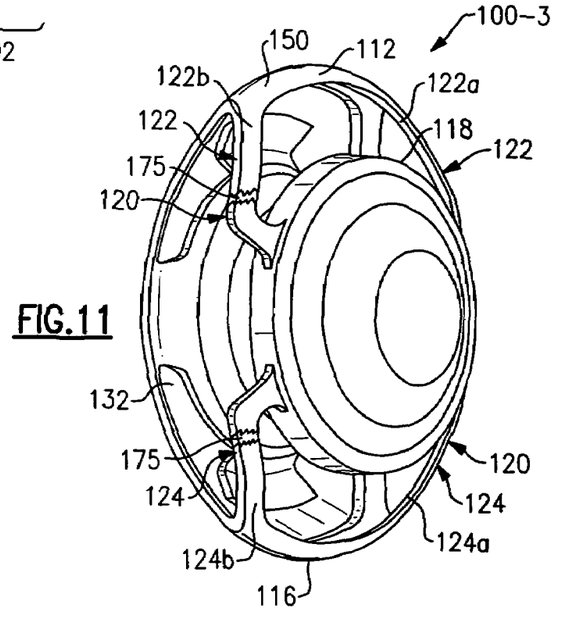
FIG. 11 is a rear perspective view of the A-IOL illustrated in FIG. 8.

FIGS. 9-11 depict another aspect of an A-IOL embodiment 100-3. A-IOL 100-3 is modeled, in part, after the accommodating intraocular lens disclosed in U.S. Pat. No. 6,858,040, the disclosure of which is hereby incorporated by reference in its entirety to the fullest possible extent allowed by applicable laws and rules. With reference to FIG. 9, a set of axes is included to illustrate the sense of directional terminology that will be used to describe various features of the A-IOL 100-3. The terms anterior and posterior have the same meanings as set forth herein above. The terms "left" and "right" refer to the directions shown on the lateral axis, which is orthogonal to the optical axis. In addition, the terms "upper" and "lower" refer to the directions depicted on the transverse axis, which is orthogonal to both the optical axis and the lateral axis. As with A-IOL 100-1, A-IOL 100-3 may rotate about, or may be displaced along, the optical axis during use without detracting from the performance of the lens. Should the A-IOL 100-3 be so rotated about the optical axis, the transverse axis may no longer have an upper-lower orientation and the lateral axis may no longer have a left-right orientation, but the lens system will continue to function as it would when oriented as depicted in FIG. 9.

As best seen in FIG. 11, the A-IOL 100-3 has an anterior segment 102 that is anterior or forward of the line A-A (which represents a plane substantially orthogonal to the optical axis and intersecting first and second apical regions 112, 116) and a posterior segment 104, which is posterior or rearward of the line A-A. The anterior segment 102 comprises an anterior optic 106 and an anterior biasing portion 108 of compressible haptic 150. The compressible haptic 150 further comprises an anterior translation member 110, which extends from the anterior optic 106 to the upper apical region 112 and from the anterior optic 106 to the lower apical region 116. The circumferential diameter of the apical region of the compressible haptic 150 defines the nominal overall diameter, D, of the A-IOL 100-3. A deformation feature 175A, of the various forms described herein above, is located in a portion of the anterior translation member 110. The deformation feature 175A will allow the nominal overall diameter of the A-IOL 100-3 to vary between D and a Dmin value in response to variations in capsular bag dimensions as discussed above, without substantially changing the optic separation distance absent an intended accommodating force acting on the A-IOL.

In the illustrative aspect as shown in FIG. 9, the anterior translation member 110 includes right arm regions 110a, 114a and left arm regions 110b, 114b. One or more deformation features 175A will be located in the right and left arm regions. In alternative aspects, the anterior translation member 110 may comprise a single arm or more than two arm regions, which would include a deformation feature to alter the nominal overall diameter of the A-IOL 100-3.

As best seen in FIGS. 10 and 11, the posterior segment 104 of A-IOL 100-3 includes a posterior optic 118 and a posterior biasing portion 120 of compressible haptic 150. The compressible haptic 150 further comprises a posterior translation member 122 extending from the posterior optic 118 to the upper apical region 112 and from the posterior optic 118 to the lower apical region 116. A deformation feature 175P is located in a portion of the posterior translation member 122.

Similar to the anterior translation member, the posterior translation member 122 may include right arm regions 122a, 124a and left arm regions 122b, 124b. One or more deformation features 175P will be located in the right and left arm regions. Alternatively, the posterior translation member 122 may comprise a single arm or more than two arm regions, which include deformation features to similarly allow variance in the nominal overall diameter of the A-IOL 100-3 without substantially changing the optic separation distance absent an intended accommodating force acting on the A-IOL.

In the exemplary A-IOL 100-3 shown in FIG. 10, the anterior biasing portion 108 and the posterior biasing portion 120 are configured symmetrically with respect to the plane A-A as the A-IOL 100-3 is viewed from the side. As used herein to describe the biasing portions 108, 120, "symmetric" or "symmetrically" means that, as the lens system 100-3 is viewed from the side, the anterior translation member 110 and the posterior translation member 122 extend from the upper apical region 112, and from the lower apical region 116, at substantially equal anterior biasing angles $\theta 1$, $\theta 3$, and posterior biasing angles $\theta 2$, $\theta 4$, with respect to the line A-A (which, again, represents the edge of a plane which is substantially orthogonal to the optical axis and intersects the upper and lower apices 112, 116). Alternative or asymmetric configurations of the compressible haptic 150 is possible, as a person skilled in the art will appreciate. It should be further noted that a symmetric configuration of the biasing portions 108, 120 does not dictate symmetric positioning of the optics 108, 118 with respect to the line A-A; in the illustrative embodiment shown in FIG. 10, the anterior optic 106 is closer to the line A-A than is the posterior optic 118.

As is the case with A-IOL 100-1, the anterior and posterior biasing portions 108, 120 of compressible haptic 150 function in a spring-like manner to permit the anterior optic 106 to translate relative to posterior optic 118 along the optical axis. The biasing portions bias the optics apart so that they separate to the natural, accommodated position of A-IOL 100-3 as shown in FIG. 10. The optics 106, 118 may be moved toward each other in response to a ciliary muscle force to provide an unaccommodated position by applying appropriate forces upon the anterior and posterior portions 102, 104.

The foregoing description of the embodiments of the invention have been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

I claim:

1. A multi-component accommodating intraocular lens (A-IOL), comprising:
    an anterior optical element;
    a posterior component; and
    a plurality of haptics which includes at least one compressible haptic that is coupled to at least a portion of the anterior optic at a first location and at least a portion of the posterior component at a second location, the at least one compressible haptic comprising a deformation feature having a valley and the at least one compressible haptic having a curvilinear shape between the deformation feature and at least one of the first location and the second location,
    an inner surface of the compressible haptic, exclusive of said deformation feature, defining an inner profile, the valley extending radially inwardly relative to said inner profile and the valley being disposed radially inward of the inner profile
    wherein the A-IOL has an equator extending through the plurality of haptics midway between the anterior optic and the posterior component, the deformation feature being located closer to the anterior optic than to the equator.

2. The A-IOL of claim 1, wherein the at least one compressible haptic has an anterior end region that joins the at least a portion of the anterior optic, a posterior end region that joins the at least a portion of the posterior component and a central region defining a nominal overall diameter, D, in an as-molded state.

3. The A-IOL of claim 2, wherein the A-IOL has a reduced diameter, $D_{min}$, when the deformation feature is in a deformed state, further wherein the A-IOL is configured such that a separation distance between the anterior optical element and the posterior component remains substantially unchanged as the deformation feature is deformed over the range of $D_{min}$ to D absent an intended accommodating force applied to the A-IOL.

4. The A-IOL of claim 3, wherein $D_{min}$ is in the range between about 80% to 95% of the nominal overall diameter D.

5. The A-IOL of claim 2, wherein the deformation feature is in the form of a semi-continuous gap.

6. The A-IOL of claim 5, wherein the semi-continuous gap has an undeformed gap dimension in a range between about 500 to 1000 microns.

7. The A-IOL of claim 6, wherein the undeformed gap dimension is about 750 microns.

8. The A-IOL of claim 5, wherein the semi-continuous gap is a squared or rounded U-shaped gap.

9. The A-IOL of claim 5, wherein the semi-continuous gap is a V-shaped gap.

10. The A-IOL of claim 5, wherein the semi-continuous gap is a W-shaped gap.

11. The A-IOL of claim 5, wherein the semi-continuous gap is a C-shaped gap.

12. The A-IOL of claim 5, wherein the semi-continuous gap is an M-shaped gap.

13. The A-IOL of claim 2, wherein the at least one compressible haptic includes an anterior translation member extending between an apical central region of the at least one compressible haptic and the anterior optic component and a posterior translation member extending between the apical central region of the at least one compressible haptic and the posterior component, wherein the a deformation feature is located in the anterior translation member.

14. The A-IOL of claim 13, wherein the anterior translation member includes a right arm and a left arm.

15. The A-IOL of claim 14, wherein the deformation feature is located in at least one of the right arm and the left arm.

16. The A-IOL of claim 13, wherein the posterior translation member includes a right arm and a left arm.

17. The A-IOL of claim 16, wherein the deformation feature is located in at least one of the right arm and the left arm.

18. The A-IOL of claim 2, wherein the deformation feature is configured and arranged to provide a hard stop, thereby determining the minimum lens separation distance between the first and second optical elements.

19. The A-IOL of claim 1, wherein the at least one compressible haptic comprises a plurality of connectable pieces.

20. The A-IOL of claim 19, wherein the plurality of connectable pieces include an anterior portion connected to the anterior optic and a posterior portion connected to the posterior component.

21. The A-IOL of claim 1, wherein the at least one compressible haptic is smooth and continuous between the deformation region and the anterior end region of the at least one compressible haptic.

22. The A-IOL of claim 1, wherein the at least one compressible haptic is smooth and continuous between the deformation region and the posterior end region of the at least one compressible haptic.

23. The A-IOL of claim 1, wherein the plurality of haptics comprises a plurality of compressible haptics.

24. The A-IOL of claim 23, wherein the plurality of compressible haptics are equally spaced about the anterior and posterior optics.

25. The A-IOL of claim 24, wherein the plurality of compressible haptics consists of three compressible haptics.

26. The A-IOL of claim 1, wherein the A-IOL is of unitary construction.

27. The A-IOL of claim 1, wherein the at least one haptic has a curvilinear shape between the first location and the second location, exclusive of the deformation feature, so as to conform to a surface of a capsular bag except at the deformation feature.

28. The A-IOL of claim 27, wherein the at least one compressible haptic has a curvilinear shape between the deformation feature and the other of the first location and the second location.

29. The A-IOL of claim 1, wherein the at least one compressible haptic is an integrated structure between the first location and the second location.

30. The A-IOL of claim 1, wherein the at least one compressible haptic is a monolithic structure between the first location and the second location.

31. The A-IOL of claim 1, wherein the posterior component comprises a posterior optical element.

32. A multi-component accommodating intraocular lens (A-IOL), comprising:
an anterior optical element;
a posterior component; and
a plurality of haptics which includes at least one compressible haptic that is coupled to at least a portion of the anterior optic at a first location and at least a portion of the posterior component at a second location, the at least one compressible haptic comprising a deformation feature having a valley and the at least one compressible haptic having a curvilinear shape between the deformation feature and at least one of the first location and the second location,
an inner surface of the compressible haptic, exclusive of said deformation feature, defining an inner profile, the valley extending radially inwardly relative to said inner profile and the valley being disposed radially inward of the inner profile
wherein the A-IOL has an equator extending through the plurality of haptics midway between the anterior optic and the posterior component, the deformation feature being located closer to the posterior component than to the equator.

33. The A-IOL of claim 32, wherein the at least one compressible haptic is a monolithic structure between the first location and the second location.

34. The A-IOL of claim 32, wherein the posterior component comprises a posterior optical element.

* * * * *